United States Patent [19]

Mukai

[11] Patent Number: 5,045,324

[45] Date of Patent: Sep. 3, 1991

[54] PASTY DIALYZING COMPOSITION FOR PERFUSING ARTIFICIAL KIDNEY SYSTEMS AND PROCESS FOR PREPARING SAME

[75] Inventor: Hisao Mukai, Naruto, Japan

[73] Assignee: Tomita Pharmaceutical Co., Ltd., Tokushima, Japan

[21] Appl. No.: 441,604

[22] Filed: Nov. 27, 1989

[30] Foreign Application Priority Data

Nov. 28, 1988 [JP] Japan .............................. 63-301419

[51] Int. Cl.$^5$ ...................... A61K 33/14; A61K 33/00
[52] U.S. Cl. .................................... 424/678; 424/679; 424/680; 424/681; 424/717
[58] Field of Search ............... 424/678, 679, 680, 681, 424/717

[56] References Cited

U.S. PATENT DOCUMENTS 4,756,838  7/1988  Veltman ............................. 424/680

OTHER PUBLICATIONS

Chem. Abst. 97: 98403j (1982), Tomita.
Chem. Abst. 104: 24223 (1986), Suzuki.

*Primary Examiner*—Frederick E. Waddell
*Assistant Examiner*—Zohreh A. Fay
*Attorney, Agent, or Firm*—Larson and Taylor

[57] ABSTRACT

The invention provides a pasty composition for perfusing artificial kidney systems for dialysis, the composition comprising about 30 to about 70% by weight of solid electrolyte components consisting of NaCl, KCl, $CaCl_2$, $MgCl_2$ and $CH_3COONa$ and about 70 to about 30% by weight of water, and the composition having a viscosity of about 1,000 to about 7,000 cps at 25° C., and also provides a process for preparing a pasty composition for perfusing artificial kidney systems for dialysis, the process comprising the steps of uniformly mixing NaCl, KCl, $CaCl_2$, $MgCl_2$ and $CH_3COONa$, adding water and finely dividing the mixture.

10 Claims, 1 Drawing Sheet

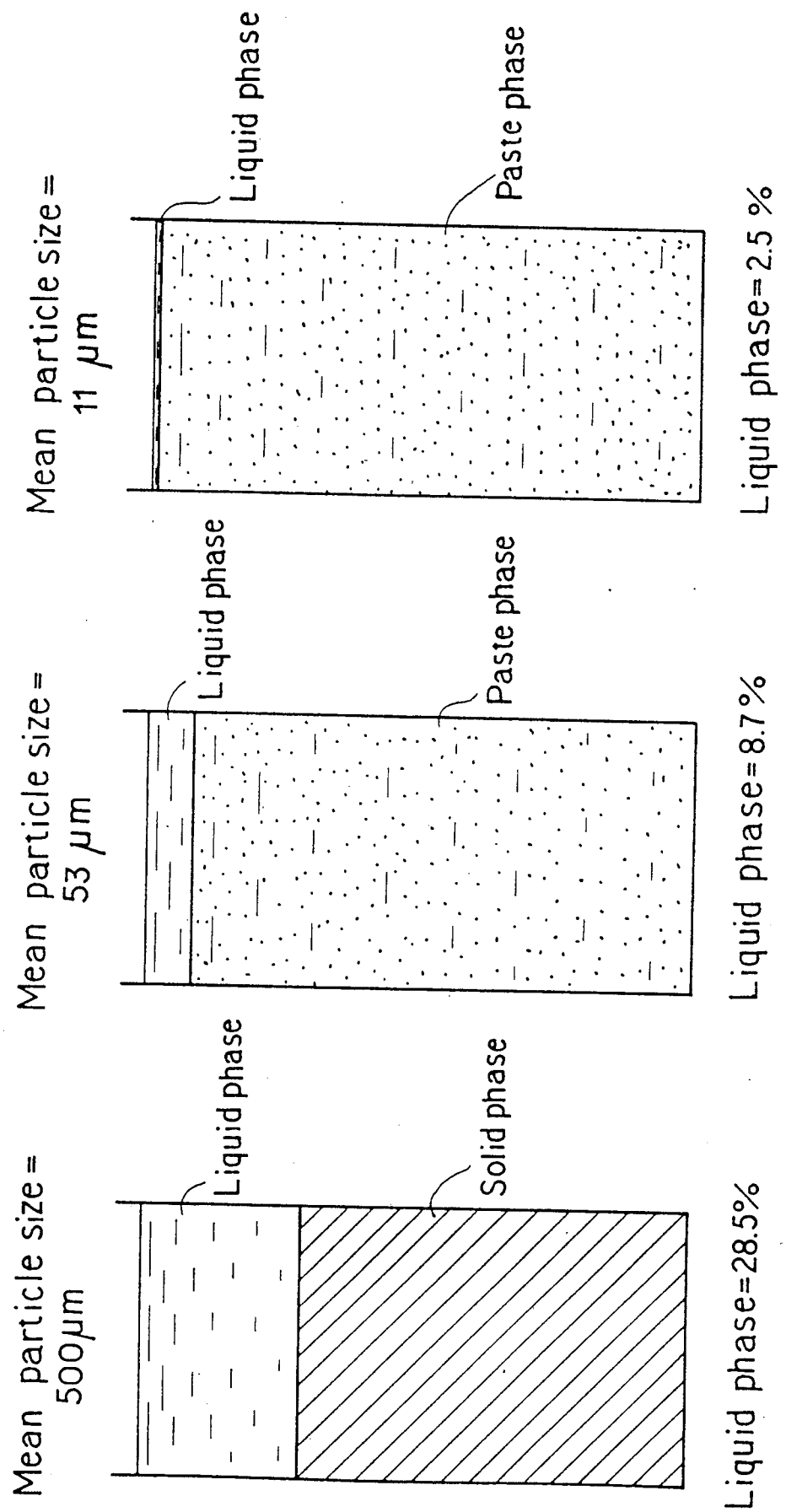

PASTY DIALYZING COMPOSITION FOR PERFUSING ARTIFICIAL KIDNEY SYSTEMS AND PROCESS FOR PREPARING SAME

FIELD OF THE INVENTION

The present invention relates to a novel pasty composition for perfusing artificial kidney systems for dialysis and a process for preparing the composition.

BACKGROUND OF THE INVENTION

Dialyzing fluids for perfusing artificial kidney systems (hereinafter referred to merely as "dialyzing fluid" unless otherwise indicated) currently available are roughly classified into acetate-containing dialyzing fluids and bicarbonate-containing dialyzing fluids.

The acetate-containing dialyzing fluids and bicarbonate-containing dialyzing fluids ready for use usually have the following compositions.

| (A) Acetate-containing dialyzing fluids | |
|---|---|
| Na | 126–145 mEq/l |
| K | 1.5–3.0 mEq/l |
| Ca | 2.5–4.0 mEq/l |
| Mg | 1.0–1.5 mEq/l |
| Cl | 98–108 mEq/l |
| $CH_3COO$ | 30–42.5 mEq/l |
| Glucose | 0–300 mg/dl |
| (B) Bicarbonate-containing dialyzing fluids | |
| Na | 135–140 mEq/l |
| K | 0–4.0 mEq/l |
| Ca | 2.5–3.5 mEq/l |
| Mg | 1.0–1.5 mEq/l |
| Cl | 106–107.5 mEq/l |
| $CH_3COO$ | 4–9 mEq/l |
| $HCO_3$ | 27.5–35 mEq/l |

Commercially available acetate-containing dialyzing fluids comprise in combination a concentrated dialyzing fluid and glucose either contained therein or provided separately as a second fluid and are diluted with water before use to give the composition of dialyzing fluid (A).

Commercially available bicarbonate-containing dialyzing fluids comprise in combination a concentrated dialyzing fluid and sodium bicarbonate provided separately as a second fluid and are diluted with water before use to give the composition of dialyzing fluid (B).

These commercially available concentrated dialyzing fluids are usually contained in a container of polyethylene or the like having a volume of about 10-l volume, consequently entailing numerous problems on storing space, difficulty in transport and like handling. Further the above concentrated dialyzing fluids readily undergo changes in pH or in composition during storage and thus are difficult to adjust to the desired pH before use and to provide with the intended composition, hence problematic also in quality stability.

To overcome these problems, we conducted extensive research and developed a process for producing a dialyzing powder by spray drying method using an aqueous solution of electrolyte compounds similar in composition to the dialyzing fluid (A) or (B) (without glucose) (Japanese Examined Patent Publication No. 34248/1982). We also developed a process for producing a bicarbonate-containing dialyzing powder, the process comprising pulverizing sodium chloride as the chief component among electrolyte compounds to particles of about 20 to about 30 μm, spraying glacial acetic acid over the particles for adsorption, and mixing the particles with other electrolytic compounds (Japanese Examined Patent Publication No. 27246/1983). The dialyzing powders of mixed electrolytic compounds obtained by these processes obviate the storing-space and handling problems, but raise other problems on producing process, quality, storage, etc. as described below.

The dialyzing powders obtained by the spray-drying method are irregular in water content and particle size. Particularly the bicarbonate-containing dialyzing powders are difficult to adjust to the desired pH.

The method spraying the glacial acetic acid over the sodium chloride powder for adsorption results in emission of offensive odor and thus in deterioration of work environment, and entails difficulty in eliminating the irregularity in amounts of minor components in the production lot.

The dialyzing powders are prone to change in pH. And NaCl, KCl, $MgCl_2$, $CaCl_2$ and the like for use as the active components have the property of solidifying on absorption of moisture, tending to solidify during storage. After solidification, the dialyzing product becomes difficult to dissolve before use.

Moreover, loss of powder is likely to occur due to scattering during the formation of an aqueous solution of powder.

SUMMARY OF THE INVENTION

It is an object of the present invention to provide an acetate-containing dialyzing composition and a bicarbonate-containing dialyzing composition which are easy to store and to handle.

It is another object of the invention to provide an acetate-containing dialyzing composition and a bicarbonate-containing dialyzing composition both excellent in the ability to retain a quality stability for a long term.

It is a further object of the invention to provide an acetate-containing dialyzing composition and a bicarbonate-containing dialyzing composition both free of the foregoing troubles during production.

Other objects and features of the invention will become apparent from the following description.

According to the present invention, there is provided a pasty composition for perfusing artificial kidney systems for dialysis, the composition comprising about 30 to about 70% by weight of a solid electrolyte component consisting of NaCl, KCl, $CaCl_2$, $MgCl_2$ and $CH_3COONa$ and about 70 to about 30% by weight of water, and the composition having a viscosity of about 1,000 to about 7,000 cps at 25° C.

According to the invention, there is also provided a process for preparing a pasty composition for perfusing artificial kidney systems for dialysis, the process comprising the steps of adding microfine NaCl powder to an aqueous solution of KCl, $CaCl_2$, $MgCl_2$ and $CH_3COONa$ and kneading the mixture.

According to the invention, there is further provided a process for preparing a pasty composition for perfusing artificial kidney systems for dialysis, the process comprising the steps of uniformly mixing NaCl, KCl, $CaCl_2$, $MgCl_2$ and $CH_3COONa$, adding water to the mixture and finely dividing the mixture.

To overcome said problems of the conventional concentrated dialyzing solutions and dialyzing powders, we conducted extensive research and found that a quality-stable dialyzing composition can be prepared in a pasty form by a simple process. The present invention has been accomplished on the basis of this novel finding.

BRIEF DESCRIPTION OF THE DRAWING

FIGURE 1 schematically shows the phase changes of three pasty dialyzing products prepared using three kinds of sodium chloride particles of different particle sizes and left to stand for one month.

DETAILED DESCRIPTION OF THE INVENTION

The pasty dialyzing composition of the invention comprises about 30 to about 70% by weight of solids and about 70 to about 30% by weight of water in a homogeneous state without separation between solids and liquid and has a viscosity of about 1,000 to about 7,000 cps at 25° C. The proportions of KCl, $CaCl_2$, $MgCl_2$ and $CH_3COONa$ in the solids are in such range that the ion composition in the aqueous solution prepared before use corresponds to the composition of acetate-containing dialyzing fluid (A) or bicarbonate-containing dialyzing fluid (B).

The pasty dialyzing composition of the invention is used in the same manner as conventional concentrated liquid dialyzing products or powder dialyzing products. For use, the acetate-containing dialyzing composition of the invention is supplied for use along with glucose separately provided. Before use, the dialyzing composition and glucose are dissolved in water in such ratio that the solution has the predetermined electrolyte concentration and glucose concentration. The bicarbonate-containing dialyzing composition of the invention is similarly supplied for use along with sodium hydrogencarbonate, and before use, they are made into an aqueous solution of desired concentration.

We will describe below by way of example two processes for preparing the pasty composition of the invention in detail.

1. First process

In the first process, sodium chloride is finely divided by an air classifying vertical impact mill (commercially avaialble under the trademark "micropulverizer") or like pulverizing means. It is preferred to use sodium chloride meeting the requirements of Japanese Pharmacopeia and having a mean particle size of about 500 μm. The sodium chloride is pulverized to a particle size of up to about 105 μm, preferably up to about 30 μm. When the microfine sodium chloride powder is over 105 μm in particle size, the finally obtained product tends to assume not a homogeneous pasty form, but a suspension form. Such heterogeneous composition is prone to separation between solids and liquid during storage, making it difficult to take out of a container or to achieve the desired dilution before use and tending to give dilute solutions irregular in composition. The finely divided sodium chloride may be further classified by a micron-separator or like means to remove coarse particles and to obtain particles of uniform particle size.

Other electrolyte compounds than NaCl are used in the ratio corresponding to the composition of dialyzing fluid (A) or (B) and are dissolved in water in an amount equal to about 40 to about 100% of the weight of the sodium chloride.

Electrolyte compounds other than NaCl used include KCl, $CaCl_2$ (optionally hydrate), $MgCl_2$ (optionally hydrate) and $CH_3COONa$ (optionally hydrate).

The proportions of the electrolyte compounds are in such range that the aqueous solution prepared before use has the ion composition of dialyzing fluid (A) or (B). Typical proportions are about 50.0 to about 90.0% by weight of NaCl, 0 to about 5.0% by weight of KCl, about 1.5 to about 4.0% by weight of $CaCl_2.2H_2O$, about 1.0 to about 3.0% by weight of $MgCl_2.6H_2O$ and about 4.0 to about 45.0% by weight of $CH_3COONa.3H_2O$.

Subsequently the microfine sodium chloride powder prepared above is charged to a mixer and the aqueous solution of electrolyte compounds are added dropwise while fully mixed and ground to give a pasty product. The mixing is continued until the mixture becomes homogeneous and pasty. When required, a plurality of mixers with different mixing capabilities may be sequentially used to effect premixing and fine mixing. In mixing, glacial acetic acid may be added to concurrently carry out adjustment of pH.

2. Second process

In the second process, NaCl and other electrolyte compounds are used in the ratio corresponding to the composition of dialyzing fluid (A) or (B) and are diluted with water in an amount equal to about 40 to about 100% of the weight of NaCl. The mixture is charged to a mixer and is mixed and ground into a paste in the same manner as in the first process by the mixer. At the mixing step, the pH may be adjusted with the addition of acetic acid as in the first process. The mixing operation may be performed on sequential basis employing a plurality of mixers as in the first process.

In the second process, pulverization of NaCl to be used and selection of kinds and proportions of other electrolyte compounds are done in the same manner as in the first process.

Of the two processes, the first process is preferred in view of simplified procedure, stabilized production of higher quality product and ease of production control.

Preferred proportions of electrolyte compounds in the pasty acetate-containing dialyzing composition of the invention are about 50 to about 70% by weight of NaCl, about 1.0 to about 5.0% by weight of KCl, about 1.0 to about 4.0% by weight of $CaCl_2.2H_2O$, about 1.0 to about 3.0% by weight of $MgCl_2.6H_2O$ and about 25.0 to about 45.0% by weight of $CH_3COONa.3H_2O$. The predetermined amount of glucose solution is conjointly used with the acetate-containing dialyzing composition of the invention as conventionally done.

Preferred proportions of electrolyte compounds in the bicarbonate-containing dialyzing composition of the invention are about 75.0 to about 90.0% by weight of NaCl, 0 to about 4.0% by weight of KCl, about 1.5 to about 4.0% by weight of $CaCl_2.2H_2O$, about 1.0 to about 3.0% by weight of $MgCl_2.6H_2O$, about 2.0 to about 12.0 by weight of $CH_3COONa.3H_2O$ and about 1.0 to about 4.0% by weight of glacial acetic acid. The predetermined amount of bicarbonate solution is conjointly used with the bicarbonate-containing dialyzing composition of the invention.

In accordance of the present invention, the following results can be achieved.

(1) The pasty dialyzing composition of the invention facilitates storage, transportation and handling because it is reduced in volume and weight to approximately ⅓ to 1/5 the volume and weight of the conventional concentrated dialyzing fluids.

(2) With a pasty form, the dialyzing composition of the invention causes no solidification on absorption of moisture unlike dialyzing powders. Consequently the composition can be easy to take out of a container and to dilute, and can avoid loss of powder due to scattering.

(3) With high stability, the pasty dialyzing composition of the invention is free of variation in composition of electrolyte ions during storage so that the composition of the invention, diluted before use, becomes a dialyzing solution constant in composition and pH.

(4) The pasty dialyzing composition of the invention can be produced with ease in a short time and is amenable to multikind and mass production.

(5) The pasty dialyzing composition of the invention can be produced with simple manufacturing equipment through simplified procedure at significantly reduced costs.

EXAMPLES

The following examples illustrate the invention in further detail.

EXAMPLE 1

Sodium chloride (NaCl) meeting the requirements of Japanese Pharmacopeia was pulverized and the obtained fine particles were classified to give a microfine powder of 10 to 20 $\mu$m in mean particle size.

To 40 kg of distilled water were added with stirring potassium chloride of Japanese Pharmacopeia grade (2.537 kg), calcium chloride ($CaCl_2.2H_2O$) of Japanese Pharmacopeia grade (3.513 kg), magnesium chloride ($MgCl_2.6H_2O$) of Japanese Pharmacopeia grade (2.069 kg) and sodium acetate ($CH_3COONa.3H2O$) of Japanese Pharmacopeia grade (11.165 kg), giving an aqueous solution of electrolyte compounds.

Next, a 79.048 kg quantity of the obtained microfine powder of sodium chloride was fed to a mixer and the aqueous solution of electrolyte compounds was gradually charged to the mixer to effect kneading, giving a pasty product (3,400 cps in viscosity as determined by Brookfield viscometer at 25° C.).

About 1.66 kg of acetic acid was added to the obtained pasty product and the mixture was kneaded by a wet mixer to obtain a pasty bicarbonate-containing dialyzing material.

Three 10 g portions of the obtained bicarbonate-containing dialyzing material were weighed out for use as test specimens and were analyzed. Table 1 below shows the results.

TABLE 1

|  | Specimen 1 | Specimen 2 | Specimen 3 |
| --- | --- | --- | --- |
| NaCl | 57.04% | 57.08% | 57.01% |
| KCl | 1.92% | 1.88% | 1.90% |
| $CaCl_2.2H_2O$ | 2.56% | 2.58% | 2.56% |
| $MgCl_2.6H_2O$ | 1.39% | 1.40% | 1.38% |
| $CH_3COON_a.3H_2O$ | 6.98% | 7.11% | 7.05% |
| $H_2O$ | 30.11% | 29.95% | 30.10% |
| pH (5% solution) | 4.51 | 4.50 | 4.51 |

Table 1 shows that the obtained pasty bicarbonate-containing dialyzing composition of the invention had a homogeneous composition.

The obtained bicarbonate-containing dialyzing composition was easy to handle and underwent no change in composition or pH even after 6-month storage in a polyethylene container. A slight separation of liquid phase occurred in the paste, but the paste was easily restored to the homogeneous state when wholly stirred.

The obtained bicarbonate-containing dialyzing composition was easily dissolved in the predetermined amount of water and the solution was usable directly for bicarbonate dialysis.

EXAMPLE 2

Sodium chloride (NaCl) meeting the requirements of Japanese Pharmacopeia was pulverized and the obtained fine particles were classified to give a microfine powder of 10 to 20 $\mu$m in mean particle size.

To 45 kg of distilled water were added with stirring potassium chloride of Japanese Pharmacopeia grade (1.16 kg), calcium chloride ($CaCl_2.2H_2O$) of Japanese Pharmacopeia grade (1.45 kg), magnesium chloride ($MgCl_2.6H_2O$) of Japanese Pharmacopeia grade (1.19 kg) and sodium acetate ($CH_3COONa.3H_2O$) of Japanese Pharmacopeia grade (35.28 kg), giving an aqueous solution of electrolyte compounds.

Next 45.27 kg of the obtained microfine sodium chloride powder was placed into a mixer and the aqueous solution of electrolyte compounds was gradually charged to the mixer to effect kneading, giving a pasty product of 5,300 cps in viscosity (as determined by Brookfield viscometer at 25° C.).

The obtained pasty product was placed into a wet mixer to perform further kneading, giving a pasty acetate-containing dialyzing composition.

About 15 kg of glucose was added to the obtained acetate-containing dialyzing composition. Three 10 g portions of the composition were weighed out for use as test specimens and analyzed. Table 2 below shows the results.

TABLE 2

|  | Specimen 1 | Specimen 2 | Specimen 3 |
| --- | --- | --- | --- |
| NaCl | 31.09% | 31.11% | 31.12% |
| KCl | 0.77% | 0.76% | 0.79% |
| $CaCl_2.2H_2O$ | 0.95% | 1.10% | 1.10% |
| $MgCl_2.6H_2O$ | 0.86% | 0.88% | 0.86% |
| $CH_3COONa.3H_2O$ | 23.99% | 24.20% | 24.18% |
| Glucose | 10.70% | 10.72% | 10.70% |
| $H_2O$ | 31.64% | 31.23% | 31.25% |

Table 2 reveals that the obtained dialyzing material of the invention had a homogeneous composition.

The obtained acetate-containing dialyzing material was easy to handle and showed no change in composition or pH even after 6-month storage in a polyethylene container. Further, a slight separation of liquid phase occurred in the pasty product, but the product was easily restored to the homogeneous state when stirred.

The acetate-containing dialyzing composition was easily dissolved in the predetermined amount of water and the solution was usable directly for acetate dialysis.

TEST EXAMPLE 1

NaCl meeting the requirements of Japanese Pharmacopeia was pulverized by a micro-pulverizer and the obtained microfine powder was classified with a micron-separator into three kinds of particles, i.e. (a) those of 105 $\mu$m or larger in particle size (500 $\mu$m in mean particle size), (b) those of 104 to 31 $\mu$m in particle size (53 $\mu$m in mean particle size) and (c) those of up to 30 $\mu$m in particle size (11 $\mu$m in mean particle size).

The pasty dialyzing product (A) (2,900 cps, 25° C.), the pasty dialyzing product (B) (3,100 cps, 25° C.) and the pasty dialyzing product (C) (3,400 cps, 25° C.) were prepared in the same manner as in Example 1 with the exception of using the three kinds of microfine NaCl powders (a), (b) and (c) each for pasty products (A), (B) and (C), respectively.

These pasty products are each placed into a 1000-l beaker (114 mm in diameter, 150 mm in height) to observe the changes in the separation between the liquid phase and the solid phase over a period of one month. The drawings, FIG. 1 A through FIG. 1 C, show the results after a lapse of one month. The figures at the bottom of the drawings represent the height (%) of the liquid phase after one month.

In the pasty product (A), the liquid phase and the solid phase began to separate immediately after admixing. The height of the liquid phase accounted for 28.5% of the height of the product in one month, while the solid phase solidified and precipitated, exhibiting no fluidity.

In the pasty product (B), a slight separation of liquid phase (height 8.7%) took place in the upper portion of the paste in one month, yet complete homogeneity as well as good fluidity was recovered by stirring.

In the pasty product (C), only a slight separation (height 2.5%) occurred between the solid phase and the liquid phase during one-month storage. The pasty product (C) remained pasty with good fluidity as a whole.

I claim:

1. A pasty composition for perfusing artificial kidney systems for dialysis, the composition comprising about 30 to about 70% by weight of solid electrolyte components consisting of NaCl, KCl, CaCl$_2$, MgCl$_2$ and CH$_3$COONa and about 70 to about 30% by weight of water, and the composition having a viscosity of about 1,000 to about 7,000 cps at 25° C.

2. An acetate-containing dialyzing fluid comprising in combination (i) a pasty composition for perfusing artificial kidney systems for dialysis, the composition comprising about 30 to about 70% by weight of solid electrolyte components consisting of NaCl, KCl, CaCl$_2$, MgCl$_2$ and CH$_3$COONa and about 70 to about 30% by weight of water, and the composition having a viscosity of about 1,000 to about 7,000 cps at 25° C., and (ii) glucose.

3. A bicarbonate-containing dialyzing fluid comprising in combination (i) a pasty composition for perfusing artificial kidney systems for dialysis, the composition comprising about 30 to about 70% by weight of solid electrolyte components consisting of NaCl, KCl, CaCl$_2$, MgCl$_2$ and CH$_3$COONa and about 70 to about 30% by weight of water, and the composition having a viscosity of about 1,000 to about 7,000 cps at 25° C., and (ii) bicarbonate.

4. A process for preparing a pasty composition for perfusing artificial kidney systems for dialysis, the process comprising the steps of adding microfine NaCl powder to an aqueous solution of KCl, CaCl$_2$, MgCl$_2$ and CH$_3$COONa and kneading the mixture.

5. A process according to claim 4 wherein the microfine NaCl powder has a particle size of up to about 105 μm.

6. A process according to claim 5 wherein the microfine NaCl powder has a particle size of up to about 30 μm.

7. A process according to claim 4 wherein the proportions of the electrolyte components are about 50.0 to about 90.0% by weight of NaCl, 0 to about 5.0% by weight of KCl, about 1.5 to about 4.0% by weight of CaCl$_2$.2H$_2$O, about 1.0 to about 3.0% by weight of MgCl$_2$.6H$_2$O and about 4.0 to about 45.0% by weight of CH$_3$COONa.3H$_2$O.

8. A process for preparing a pasty composition for perfusing artificial kidney systems for dialysis, the process comprising the steps of uniformly mixing NaCl, KCl, CaCl$_2$, MgCl$_2$ and CH$_3$COONa, adding water to the mixture and finely dividing the mixture.

9. A process according to claim 8 wherein the microfine NaCl powder has a particle size of up to about 30 μm.

10. A process according to claim 8 wherein the proportions of the electrolyte components are about 50.0 to about 90.0% by weight of NaCl, 0 to about 5.0% by weight of KCl, about 1.5 to about 4.0% by weight of CaCl$_2$.2H$_2$O, about 1.0 to about 3.0% by weight of MgCl$_2$.6H$_2$O and about 4.0 to about 45.0% by weight of CH$_3$COONa.3H$_2$O.

* * * * *